(12) United States Patent
Adams et al.

(10) Patent No.: US 9,572,755 B2
(45) Date of Patent: Feb. 21, 2017

(54) BATH SALT COMPOSITION

(71) Applicant: Reckitt Benckiser (Brands) Limited, Slough (GB)

(72) Inventors: Verity Adams, Hull (GB); Maida Ponchateau, Hull (GB); Aimee Peachey, Hull (GB); James Scott, Hull (GB)

(73) Assignee: RECKITT BENCKISER (BRANDS) LIMITED, Slough, Berkshire (GB)

( * ) Notice: Subject to any disclaimer, the term of this patent is extended or adjusted under 35 U.S.C. 154(b) by 0 days.

(21) Appl. No.: 14/897,265

(22) PCT Filed: Jun. 11, 2014

(86) PCT No.: PCT/GB2014/051799
§ 371 (c)(1),
(2) Date: Dec. 10, 2015

(87) PCT Pub. No.: WO2014/199156
PCT Pub. Date: Dec. 18, 2014

(65) Prior Publication Data
US 2016/0143823 A1   May 26, 2016

(30) Foreign Application Priority Data
Jun. 13, 2013   (GB) .................................. 1310513.5

(51) Int. Cl.
| | | |
|---|---|---|
| A61K 8/02 | (2006.01) | |
| A61K 8/11 | (2006.01) | |
| A61Q 19/10 | (2006.01) | |
| A61K 8/19 | (2006.01) | |
| A61K 8/20 | (2006.01) | |
| A61K 8/365 | (2006.01) | |
| A61K 8/41 | (2006.01) | |
| A61K 8/92 | (2006.01) | |
| A61Q 19/00 | (2006.01) | |

(52) U.S. Cl.
CPC .............. *A61K 8/11* (2013.01); *A61K 8/0225* (2013.01); *A61K 8/19* (2013.01); *A61K 8/20* (2013.01); *A61K 8/365* (2013.01); *A61K 8/41* (2013.01); *A61K 8/92* (2013.01); *A61Q 19/00* (2013.01); *A61Q 19/10* (2013.01); *A61K 2800/222* (2013.01); *A61K 2800/56* (2013.01); *A61K 2800/592* (2013.01); *A61K 2800/622* (2013.01); *A61K 2800/651* (2013.01); *A61K 2800/74* (2013.01)

(58) Field of Classification Search
None
See application file for complete search history.

(56) References Cited

U.S. PATENT DOCUMENTS

| | | | |
|---|---|---|---|
| 4,250,043 A | | 2/1981 | Jones |
| 4,675,140 A | * | 6/1987 | Sparks ..................... B01J 13/04 264/4.3 |
| 4,678,661 A | * | 7/1987 | Gergely ..................... A23L 2/40 424/44 |
| 2006/0083708 A1 | * | 4/2006 | Schwartz ............... A61K 8/965 424/74 |
| 2010/0249004 A1 | * | 9/2010 | Fack ...................... A61K 8/463 510/124 |
| 2013/0078206 A1 | | 3/2013 | Dubinchuk |

FOREIGN PATENT DOCUMENTS

| | | |
|---|---|---|
| EP | 0716851 A1 | 6/1996 |
| WO | 9622676 A1 | 8/1996 |

OTHER PUBLICATIONS

Wolfgang et al. (EP0716851 english translation).*
International Search Report in related PCT Application No. PCT/GB2014/051799, mailed Nov. 25, 2014.

* cited by examiner

*Primary Examiner* — Robert A Wax
*Assistant Examiner* — Quanglong Truong
(74) *Attorney, Agent, or Firm* — Troutman Sanders LLP; Ryan A. Schneider; Chris N. Davis

(57) ABSTRACT

The present invention is directed to a granulated composition comprising a salt encapsulated by a composition that comprises at least one wax.

21 Claims, No Drawings

BATH SALT COMPOSITION

CROSS-REFERENCE TO RELATED APPLICATIONS

This application is a US National Stage of International Application No. PCT/GB2014/051799, filed 11 Jun. 2014, which claims the benefit of GB 1310513.5, filed 13 Jun. 2013, both which are fully incorporated by reference.

The present invention is directed to a novel composition for use in a foot-soaking bath. In particular, the present invention is directed to a coated salt composition for use in a foot-soaking composition.

Foot soaking is regularly undertaken for beauty, wellbeing and therapeutic reasons, such as softening the foot, preparing the foot for further beauty treatment, relaxing or re-energising, refreshing, fragrancing, warming or cooling hot or cold feet, soothing uncomfortable or painful feet and improving blood circulation.

Soaking is typically done by placing the feet in a basin, or bucket of water at the appropriate temperature (typically about 40° C.) and leaving them for period of time for the required effect to take place. A minimum amount of time is required during soaking for the associated benefits associated to be take effect, typically ~20 mins.

Foot-treatment basins having the function of providing foot soaking or spa-type treatment are well-known.

Products are available as additives to water in order to enhance the soaking experience. These broadly fall into the categories of liquid soaking products that are diluted, or solid soaking products that are dissolve into water. Typically, these products include traditional Chinese medicines, herbal ingredients, vitamins and minerals, fragrance, other cosmetic and sensorial ingredients (including effervescent ingredients), and in some cases medicinal ingredients.

Solid products available are mainly powders, salt crystals or effervescent tablets, both commonly enhanced with fragrance and colour. Liquid foot soak products generally contain skin care ingredients, however do not give a visual or physical sensorial experience due to rapidly diluting into water and fragrance bloom is limited. Solid soaking products give a visual sensorial experience during dissolving; however, the skincare benefits are limited due to requirement for an anhydrous formulation.

Accordingly, existing compositions provide either a visually and stimulating sensorial experience with limited skincare benefit, or skincare enhancement without any visual indication of efficacy or enhancement of fragrance by effervescence.

According to the present invention there is provided a granulated composition comprising a salt encapsulated by a composition that comprises at least one wax.

The salt can be selected from the group consisting of ionic salts, most commonly sodium chloride. Any other suitable cosmetic salt can also be used, such as magnesium sulphate.

Typically the granulated composition comprises 60-70% salt.

The encapsulating composition comprises components selected such that the composition melts at a temperature of between 30-60° C. The temperature at which the composition melts can be between 40-50° C.

The encapsulating composition can be selected from the group consisting of *butyrospermum parkii*, jojoba wax, mimosa wax, sunflower wax, polyethylene fatty ethers, *Theobroma Cacao, Cocos Nucifera, Mangifera Indica*

Typically the granulated composition comprises 5-10% encapsulating composition.

The composition can further include a skin-conditioning agent. The skin-conditioning agent can be selected from the group consisting of silicones, ureas, polyquaternium polymers and polyethylene glycol ethers, natural plant oils including nut oils.

Typically the granulated composition 7-10% skin-conditioning agent.

The composition can further include one or more components that are capable of effervescing. The one or more components can be selected from sodium bicarbonate, potassium bicarbonate, sodium sesquicarbonates, citric acid (anhydrous or monohydrate), tartaric acid. Typically, the one or more effervescent components are a combination of sodium bicarbonate and citric acid.

Typically the granulated composition comprises 14-20% one or more components that in combination are capable of effervescing. The one or more components that are capable of effervescing can be selected to be a combination of an acid and a base. When the components are selected to be an acid and a base the ratio of acid:base can be selected to be from 1:2 to 2:1. A preferred ratio range is 1.5:1 to 1:1. A more preferred acid:base ratio is 1.3:1.

Typically the one or more effervescent components comprise 7-10% sodium bicarbonate and 7-10% citric acid.

The ratio of the salt:encapsulating agent can be selected to be from about 1:1 to about 10:1. A preferred ratio is about 7:1.

The ratio of the salt:skin-conditioning agent can be selected to be from about 1:1 to about 10:1. A preferred ratio is about 7:1.

The ratio of the encapsulating agent:skin-conditioning agent can be selected to be from about 0.5:1 to about 1.5:1. A preferred ratio is about 1:1.

The granulated composition can be provides with several encapsulating layers. Each of the layers can be provided with a different sensorial material. Typically, the composition is provided with layers of salt, encapsulated by a composition that comprises at least one wax, which is then coated with a skin-conditioning composition, and finally an effervescent composition.

The composition of the layers can be selected such that each layer dissolves over a pre-determined period of time. Typically, the effervescent layer dissolves over a period of up to 20 seconds.

Typically the granulated composition comprises 60-70% salt, 5-10% encapsulating composition, 7-10% urea, 7-10% sodium bicarbonate and 7-10% citric acid.

In a preferred embodiment the granulated composition comprises:

| | |
|---|---|
| Salt | 65% |
| Encapsulating composition | 8.5% |
| Urea | 9% |
| Sodium Bicarbonate | 9.92% |
| Citric acid | 7.57% |

An example embodiment of the present invention will now be described in more detail.

| Component | % w/w |
|---|---|
| Salt | 65 |
| Encapsulating composition | 8.5 |
| Urea | 9 |
| Citric acid | 9.92 |

| Component | % w/w |
|---|---|
| Sodium bicarbonate | 7.57 |
| Yellow dye | 0.012 |

The components of the encapsulating composition for coating the salt are added together and heated to 80° C. The mixture is stirred until homogenous. Urea powder was added and the resulting mixture was stirred until evenly dispersed and a paste was formed. The dye was added to the mixture and stirred until homogenous. The final mixture was added to the salt and stirred until the salt was evenly coated. The effervescent coating was prepared by grinding the sodium bicarbonate and citric acid. The effervescent coating was added to the fatty coated salt mixture, and stirring was continued whilst the final mixture was allowed to cool. The resulting particles were then ready for use.

An advantage of the present invention is that there is provided a footcare composition which gives a user an ingredients-led benefit with a dynamic effervescent action, delivered during soaking, thus providing the benefits associated with effervescence dissolution, ingredients and soaking all in one.

Further modifications can be made without departing from the scope of the invention described herein.

The invention claimed is:

1. A granulated composition comprising a salt encapsulated by an encapsulating composition that comprises at least one wax;
    wherein the granulated composition comprises:
        between 60-70% salt;
        between 7-10% urea;
        between 7-10% sodium bicarbonate; and
        between 7-10% citric acid; and
    wherein the granulated composition further comprises between 5-10% encapsulating composition.

2. The granulated composition as claimed in claim 1, wherein the encapsulating composition comprises components selected such that the encapsulating composition melts at a temperature of between 30-600° C.

3. The granulated composition as claimed in claim 1, wherein the encapsulating composition is selected from the group consisting of *butyrospermum parkii*, jojoba wax, mimosa wax, sunflower wax, polyethylene fatty ethers, *Theobroma Cacao, Cocos Nucifera*, and *Mangifera Indica*.

4. A granulated composition comprising:
    layers of salt encapsulated by an encapsulating composition that comprises at least one wax;
    a skin-conditioning composition coating the encapsulating composition; and
    an effervescent composition coating the skin-conditioning composition.

5. The granulated composition as claimed in claim 4, wherein the effervescent composition dissolves in a medium over a period of up to 20 seconds.

6. The granulated composition as claimed in claim 4, wherein the granulated composition comprises:

| Component | % w/w |
|---|---|
| Salt | 65 |
| Encapsulating composition | 8.5 |
| Urea | 9 |

| Component | % w/w |
|---|---|
| Citric acid | 9.92 |
| Sodium bicarbonate | 7.57 |

7. The granulated composition as claimed in claim 4, wherein at least one of the components capable of effervescing is selected from the group consisting of sodium bicarbonate, potassium bicarbonate, sodium sesquicarbonates, citric acid (anhydrous or monohydrate), and tartaric acid.

8. A granulated composition consisting essentially of a salt encapsulated by an encapsulating composition that comprises at least one wax, wherein the granulated composition comprises:
    between 60-70% salt;
    between 7-10% urea;
    between 7-10% sodium bicarbonate; and
    between 7-10% citric acid; and
    wherein the composition further comprises between 5-10% encapsulating composition.

9. The granulated composition as claimed in claim 8, wherein the granulated composition consists essentially of:

| Component | % w/w |
|---|---|
| Salt | 65 |
| Encapsulating composition | 8.5 |
| Urea | 9 |
| Citric acid | 9.92 |
| Sodium bicarbonate | 7.57 |

10. The granulated composition as claimed in claim 8, wherein the encapsulating composition comprises components selected such that the encapsulating composition melts at a temperature of between 30-600° C.

11. The granulated composition as claimed in claim 8, wherein the encapsulating composition is selected from the group consisting of *butyrospermum parkii*, jojoba wax, mimosa wax, sunflower wax, polyethylene fatty ethers, *Theobroma Cacao, Cocos Nucifera*, and *Mangifera Indica*.

12. The granulated composition as claimed in claim 8 further comprising two or more encapsulating layers.

13. The granulated composition as claimed in claim 8 further comprising:
    layers of salt encapsulated by the encapsulating composition;
    urea coating the encapsulating composition; and
    sodium bicarbonate and citric acid coating the urea.

14. The granulated composition as claimed in claim 8, wherein the sodium bicarbonate and citric acid dissolves in a medium over a period of up to 20 seconds.

15. A granulated composition consisting of a salt encapsulated by an encapsulating composition that comprises at least one wax, wherein the granulated composition comprises:
    between 60-70% salt;
    between 7-10% urea;
    between 7-10% sodium bicarbonate; and
    between 7-10% citric acid; and
    wherein the composition further comprises between 5-10% encapsulating composition.

16. The granulated composition as claimed in claim 15, wherein the granulated composition consists of:

| Component | % w/w |
| --- | --- |
| Salt | 65 |
| Encapsulating composition | 8.5 |
| Urea | 9 |
| Citric acid | 9.92 |
| Sodium bicarbonate | 7.57 |

17. The granulated composition as claimed in claim 15, wherein the encapsulating composition comprises components selected such that the encapsulating composition melts at a temperature of between 30-600° C.

18. The granulated composition as claimed in claim 15, wherein the encapsulating composition is selected from the group consisting of *butyrospermum parkii*, jojoba wax, mimosa wax, sunflower wax, polyethylene fatty ethers, *Theobroma Cacao, Cocos Nucifera*, and *Mangifera Indica*.

19. The granulated composition as claimed in claim 15 further comprising two or more encapsulating layers.

20. The granulated composition as claimed in claim 15 further comprising:
   layers of salt encapsulated by the encapsulating composition;
   urea coating the encapsulating composition; and
   sodium bicarbonate and citric acid coating the urea.

21. The granulated composition as claimed in claim 15, wherein the sodium bicarbonate and citric acid dissolves in a medium over a period of up to 20 seconds.

\* \* \* \* \*